United States Patent [19]

Schaller

[11] Patent Number: 5,995,580

[45] Date of Patent: Nov. 30, 1999

[54] IMAGE RECONSTRUCTION METHOD FOR A COMPUTED TOMOGRAPHY APPARATUS

[75] Inventor: Stefan Schaller, Fuerth, Germany

[73] Assignee: Siemens Aktiengesellschaft, Munich, Germany

[21] Appl. No.: 09/086,151

[22] Filed: May 28, 1998

[30] Foreign Application Priority Data

Jun. 2, 1997 [DE] Germany ............................ 197 23 095

[51] Int. Cl.$^6$ ........................................................ A61B 6/03
[52] U.S. Cl. ............................................. 378/15; 378/901
[58] Field of Search ................................... 378/4, 15, 901

[56] References Cited

U.S. PATENT DOCUMENTS

| | | | |
|---|---|---|---|
| 5,463,666 | 10/1995 | Eberhard et al. ............................ | 378/4 |
| 5,500,883 | 3/1996 | Hsiao et al. ................................. | 378/4 |
| 5,901,195 | 5/1999 | Sauer et al. ................................. | 378/4 |
| 5,901,196 | 5/1999 | Sauer et al. ................................. | 378/4 |

OTHER PUBLICATIONS

"On Two Approaches to 3D Reconstruction in NMR Zeugmatography," Marr et al., Proc. Mathematical Aspects of Computerized Tomography, Herman et al., Eds. (1980).

"Mathematical Framework of Cone Beam 3d Reconstruction via the First Derivative of the Radon Transform," Grangeat, Mathematical Methods in Tomography, Herman et al, Eds. (1991).

*Primary Examiner*—David Vernon Bruce
*Attorney, Agent, or Firm*—Hill & Simpson

[57] ABSTRACT

An exact image reconstruction method for computed tomography allows the reconstruction of a sub-volume of interest in a long subject from cone beam or pyramid beam CT data using a spiral focus path. A two-stage reconstruction process is utilized that, by line integration over the detector, first calculates 3D radon values of a sub-volume of interest defined only for the respective φ-plane for each φ-plane of a 3D spherical coordinate system. For each φ-plane, the sub-volume of interest is limited toward the exterior by the radius of the measurement field and is upwardly and downwardly limited by curved surfaces that arise by the locus of a straight line perpendicular to the φ-plane under consideration proceeding to each focus point of a spiral segment.

5 Claims, 8 Drawing Sheets

IMAGE RECONSTRUCTION METHOD FOR A COMPUTED TOMOGRAPHY APPARATUS

BACKGROUND OF THE INVENTION

1. Field of the Invention

The present invention is directed to an image reconstruction method of the type suitable for use for producing a displayed image from cone beam data or pyramidal beam data in an x-ray computed tomography apparatus.

2. Description of the Prior Art

Algorithms are known in computer tomography (CT) for the exact reconstruction of tomographic cone beam data or pyramidal beam data wherein radon values in the 3D radon space are first calculated by line integration over the two-dimensional detector (Mathematical Methods in Tomography, G. T. Herman, A. K. Louis, F. Natterer, Eds., Lecture Notes in Mathematics, Springer Verlag 1991). FIG. 1 schematically shows the focus 1 of an X-ray source that emits a pyramidal X-ray beam 2 that strikes a two-dimensional detector 3. The detector 3 is formed by a matrix of detector elements whose output signals are supplied to a computer 4 that calculates an image of the examination subject 5 therefrom and effects the playback on a monitor 6. The examination subject 5 is transirradiated from various projections. To this end, the X-ray source and the detector 3 and, thus, the X-ray beam 2 as well are rotated around the examination subject 5 around the system axis 7. The radial derivative of the radon transform is determined by integration along lines, for example the line 8, over data from detector elements lying in those lines. The identified radon value, or the identified radial derivative of the radon value, corresponds to the surface integral over the integration plane 9. On the basis of this procedure, the 3D radon values on a spherical coordinate system r, ⊖, φ in the 3D radon space are first determined from a number of projections. As described by Marr et al. in Proc. Mathematical Aspects of Computerized Tomography, Oberwolfach (FRG), 1980, G. T. Herman, F. Natterer, Eds., Springer Verlag, 1981, the subject can be reconstructed in a two-stage process proceeding from these 3D radon values. In the first step, a 2D parallel projection of the subject perpendicular to the φ-plane is generated on every φ-plane by ordinary 2D radon inversion. In the second step, the subject in this slice is reconstructed, again by ordinary 2D radon inversion on every vertical plane. This procedure is illustrated in FIG. 2. FIG. 2 shows a two-stage reconstruction algorithm according to Marr et al. First, respective 2D radon inversions are implemented on all φ-planes. As a result, a 2D parallel projection through the subject perpendicular to the φ-plane is calculated on every φ-plane. Each row or line of such a 2D parallel projection belongs to a different vertical (z-const.) plane. Using all values belonging to a vertical plane, the subject in this slice is reconstructed, again by 2D radon inversion on this vertical plane. This is implemented for all vertical planes and thus supplies the reconstructed subject volume 10.

Most of these exact reconstruction algorithms assume that the subject does not extend beyond the ray pyramid of the projection in any projection. This condition cannot be met in medical CT scanners. Other algorithms enable the reconstruction of a sub-volume of interest in a long subject when this sub-volume is bounded by two planes and the focus path contains two circular paths on these boundary surfaces (U.S. Pat. No. 5,463,666). Thus, for example, a sub-volume of interest can be reconstructed from a spiral scan when the spiral scan is supplemented by a respective circle at the top and bottom on the boundary surfaces of this sub-volume (see FIG. 3). FIG. 3 shows the reconstruction of a sub-volume 11 of interest from the examination subject 5, which is a long subject in this case, according to U.S. Pat. No. 5,463,666 with a spiral focus path 12 expanded by two circles. For calculating the plane integral corresponding to a 3D radon value, this plane—as shown in FIG. 4—is divided into a number of sub-regions, each of which is covered by a projection. The sub-area of interest of this integration plane is shown shaded in FIG. 4. It arises from the intersection of the integration plane with the sub-volume of interest. For the reconstruction of the sub-volume of interest, the plane integrals are only allowed to extend over the sub-area of interest. To that end, it is necessary that the limitation of the sub-area of interest is a straight line and that a focus position lies on this line. FIG. 4 shows the intersection lines 13 of the integration plane 9 with the limiting surfaces of the sub-volume 11 of interest. The sub-area 14 of interest is shown shaded. This sub-area 14 of the integration plane is covered by combining a number of projections.

As in FIG. 4, FIG. 5 shows the integration over the sub-area of interest shaded. In FIG. 5, however, no focus position is located on the upper boundary line of the sub-area of interest 14. Some of the rays required for the calculation of the integral over the sub-area 14 of interest are falsified by contributions of regions outside the sub-volume 11 of interest (as an example, a ray 15 is entered that also receives contributions on the section (shown bold) outside the sub-volume 11 of interest). The integral therefore cannot be formed over the sub-area 14 of interest.

In all known algorithms, a sub-volume of interest is defined, and a consistent 3D radon set is generated by limiting the plane integration to the sub-volume of interest.

U.S. Pat. No. 5,500,883 discloses a computer tomography apparatus with a cone beam or a pyramidal beam, whereby the radon values are calculated using a number of computers that divide the radon space among them such that the individual computers respectively handle regions of the radon space that are of approximately the same size. In detail, each computer handles a number of vertical planes in the radon space that are distributed over 180° in the φ-direction at identical angular spacings and that respectively contain a polar coordinate system for the radon values belonging to that vertical plane. A spiral scan is not provided.

SUMMARY OF THE INVENTION

It is an object of the present invention is to provide an exact image reconstruction method for a computer tomography apparatus for sub-volumes of interest (regions of interest) of a long subject from cone beam or pyramid beam CT data using a spiral focus path.

The above object is achieved in accordance with the principles of the present invention in an image reconstruction method for use in a computed tomography apparatus for reconstructing sub-volumes of interest of a subject employing a spiral scan with cone beam or pyramid beam geometry of the x-ray beam, wherein a twostage reconstruction process is employed which, by line integration over the radiation detector, first calculates 3D radon values of a sub-volume of interest, defined only for respective φ-plane of a 3D spherical coordinate system, this calculation being successively undertaken for each φ-plane of the 3D spherical coordinate system. The sub-volume of interest for each φ-plane is limited toward the exterior by the radius of the measurement field and is limited upwardly and downwardly by respective curved surfaces, each curved surface being produced by the locus of a straight line proceeding perpendicularly to the φ-plane and proceeding from said focus point locations positioned on a spiral segment of said spiral scan.

When the specific nature of the reconstruction process following the calculation of the radon values is taken into consideration, then it suffices when consistency of the radon values exists within each and every φ-plane.

2D parallel projections of the subject are generated from the radon values of every individual φ-plane by 2D radon inversion, i.e. every value generated in the first stage corresponds to a line integral over the subject on a line perpendicular to the φ-plane. The correctness of this line integral thus cannot be dependent on radon values of other φ-planes. It is also not required that the radon values of different φ-planes be consistent with one another.

It is thus not required that all generated radon values belong to a really existing 3D sub-volume of the subject. On the contrary, it suffices when the 3D radon values on every φ-plane respectively belong to a set of plane integrals over a sub-volume of interest, and this sub-volume can be differently defined for each angle φ. The result of this first stage of the reconstruction algorithm is a 2D parallel projection of the sub-volume of interest defined for this φ-angle perpendicular to the φ-plane.

DESCRIPTION OF THE PREFERRED EMBODIMENTS

Figure 6:
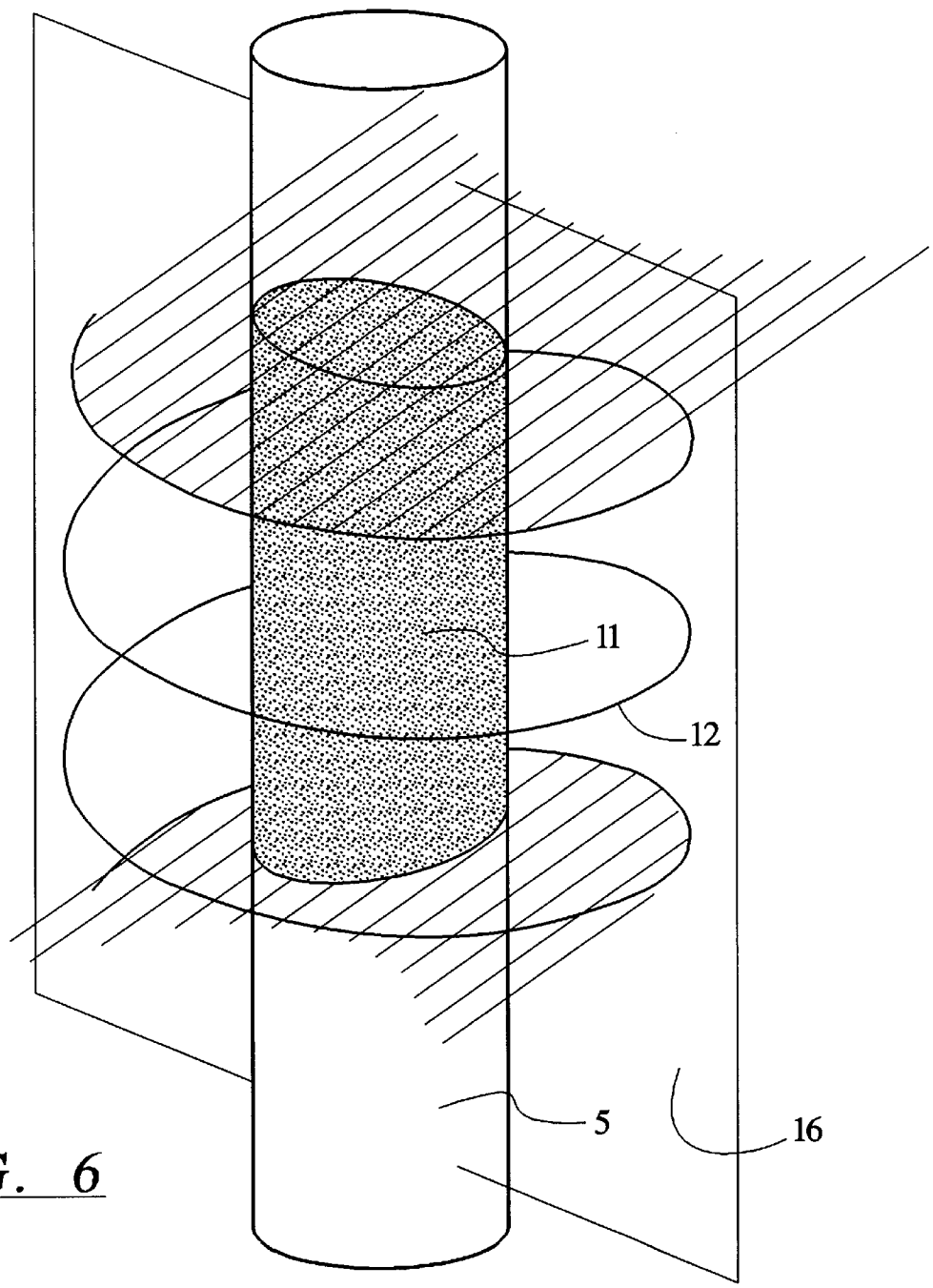
FIG. 6 is an example of the definition of the sub-volume of interest according to the invention.

In the inventive method, a separate shape of the sub-volume 11 of interest established by the shape of the spiral focus path 12 is selected so that for each φ-plane 16, the sub-volume 11 of interest is enclosed by an arbitrary, whole-numbered number of half-revolutions. The sub-volume 11 of interest is limited toward the exterior by the radius of the measurement field. Differing from known methods, the upper and lower limitations of the sub-volume 11 of interest, valid only for the φ-plane under consideration, are not respectively defined by a plane but instead by respective curved surfaces shown shaded in FIG. 6. Each curved surface is produced by the locus of a straight line proceeding perpendicularly to the φ-plane from any one focus point.

Figure 7:
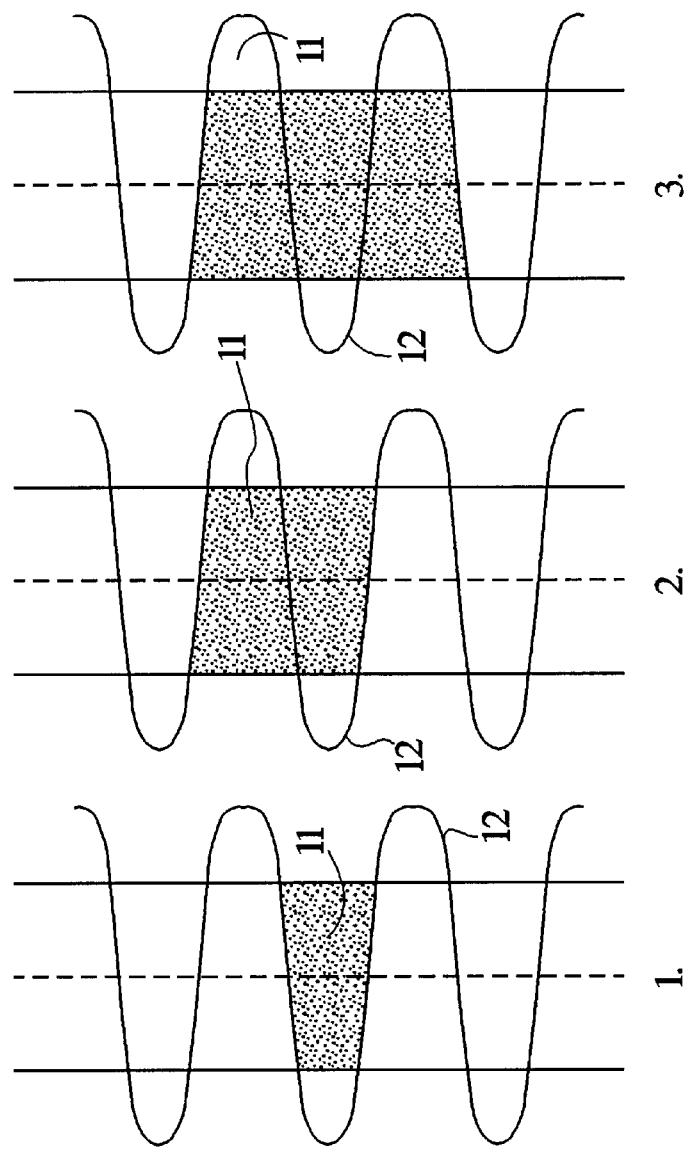
FIG. 7 is a plan view onto FIG. 6 perpendicular to the φ-plane.

In a plan view perpendicular to the respective φ-plane 16, FIG. 7 shows three possibilities for the selection of the sub-volume of interest.

Figure 1:
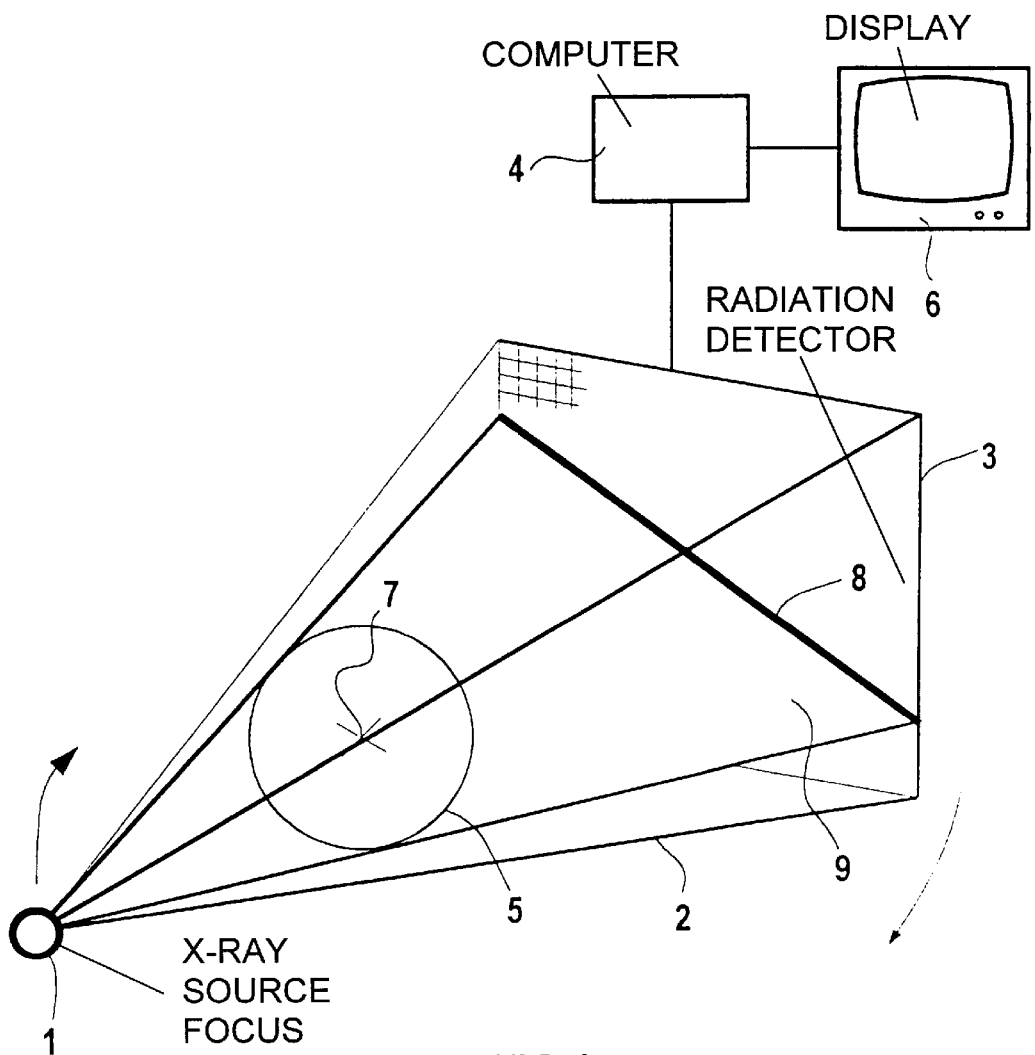
FIG. 1, as noted above, schematically illustrates the basic components of a conventional computed tomography system employing pyramidal x-ray beam geometry.
Figure 2:
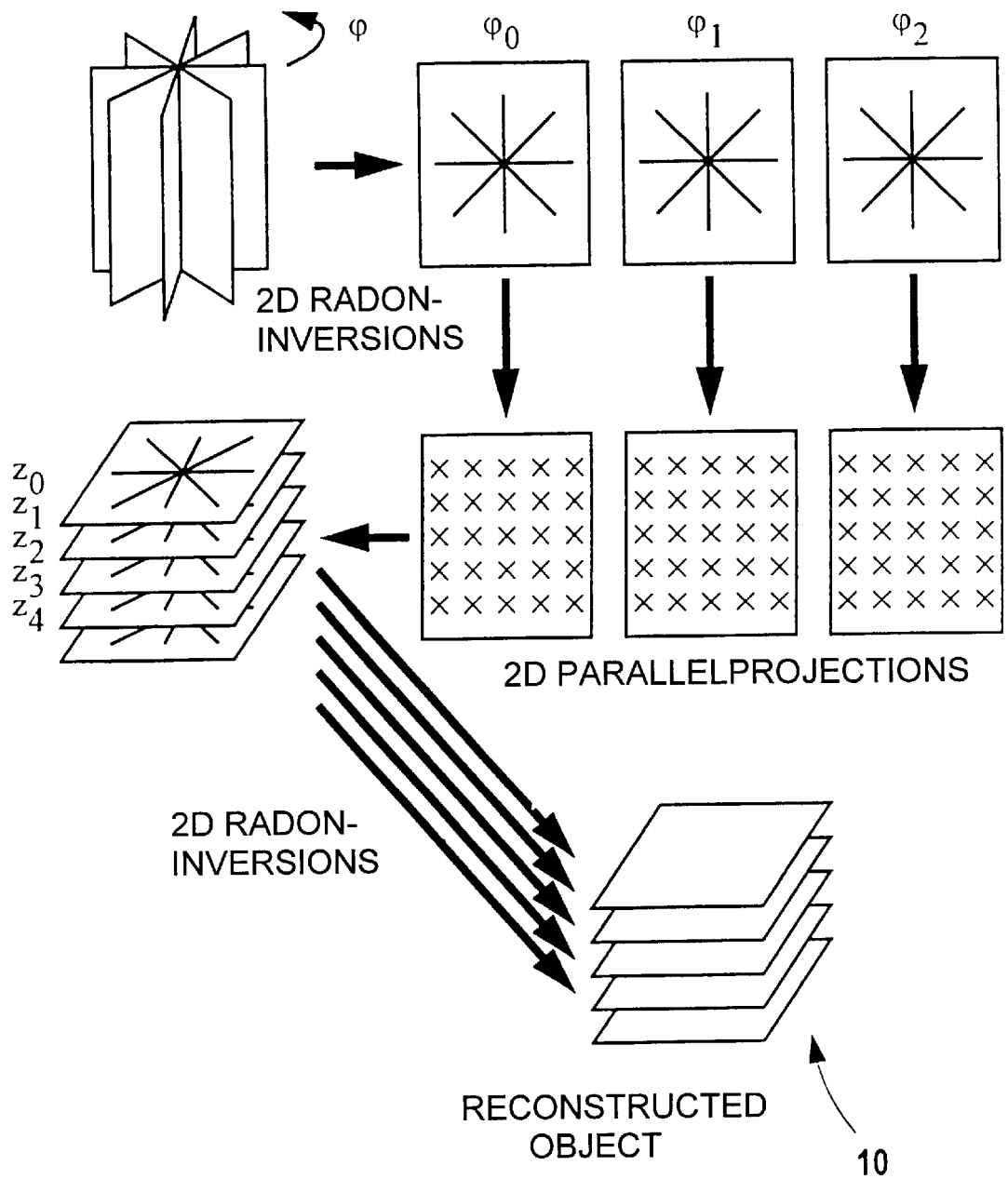
FIG. 2, as noted above, schematically illustrates the basic image reconstruction procedure in a conventional computed tomography system of the type shown in FIG. 1.
Figure 3:
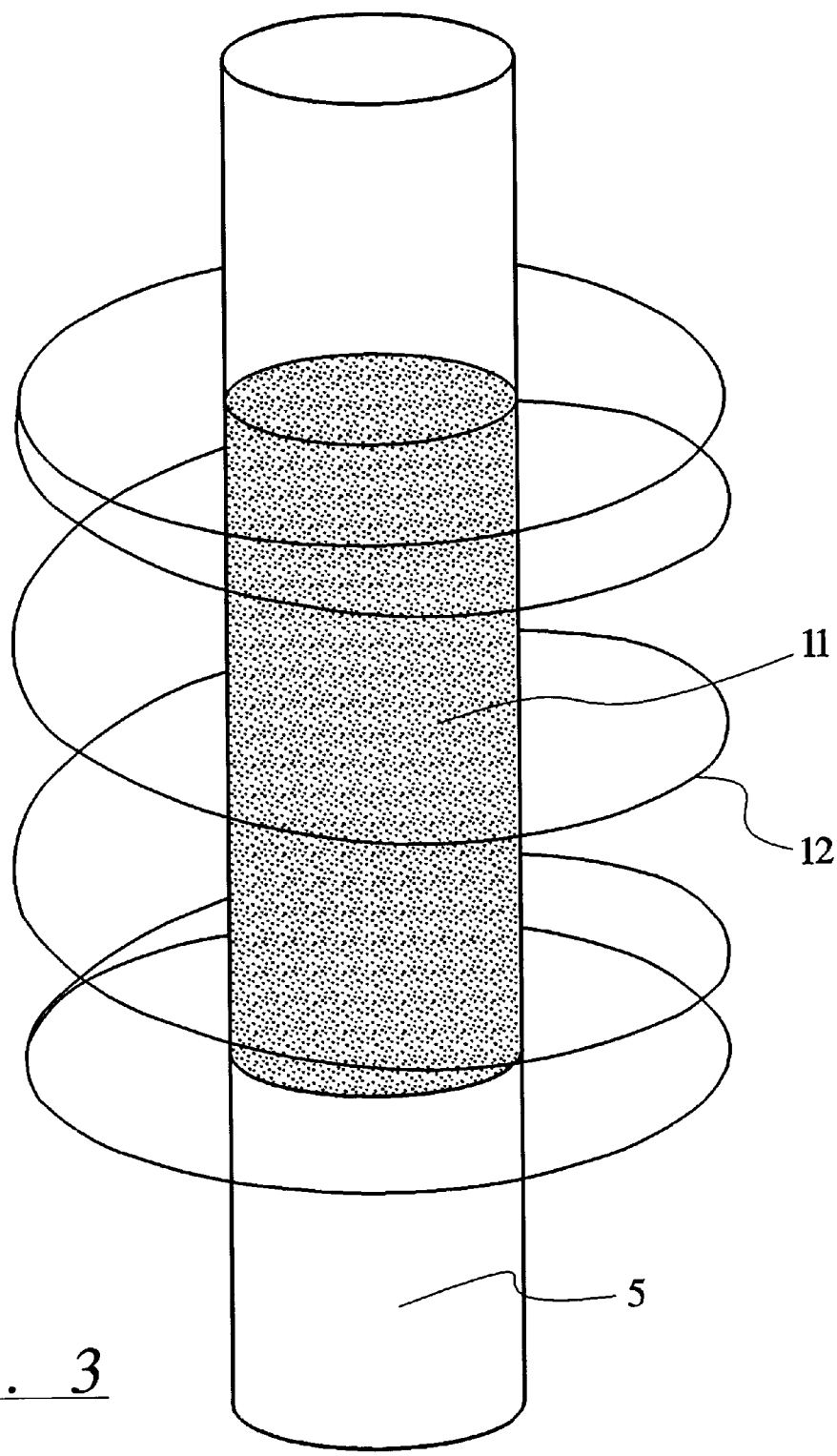
FIG. 3, as noted above, schematically illustrates the manner by which a sub-volume of interest is defined in a conventional spiral scan computed tomography system.
Figure 4:
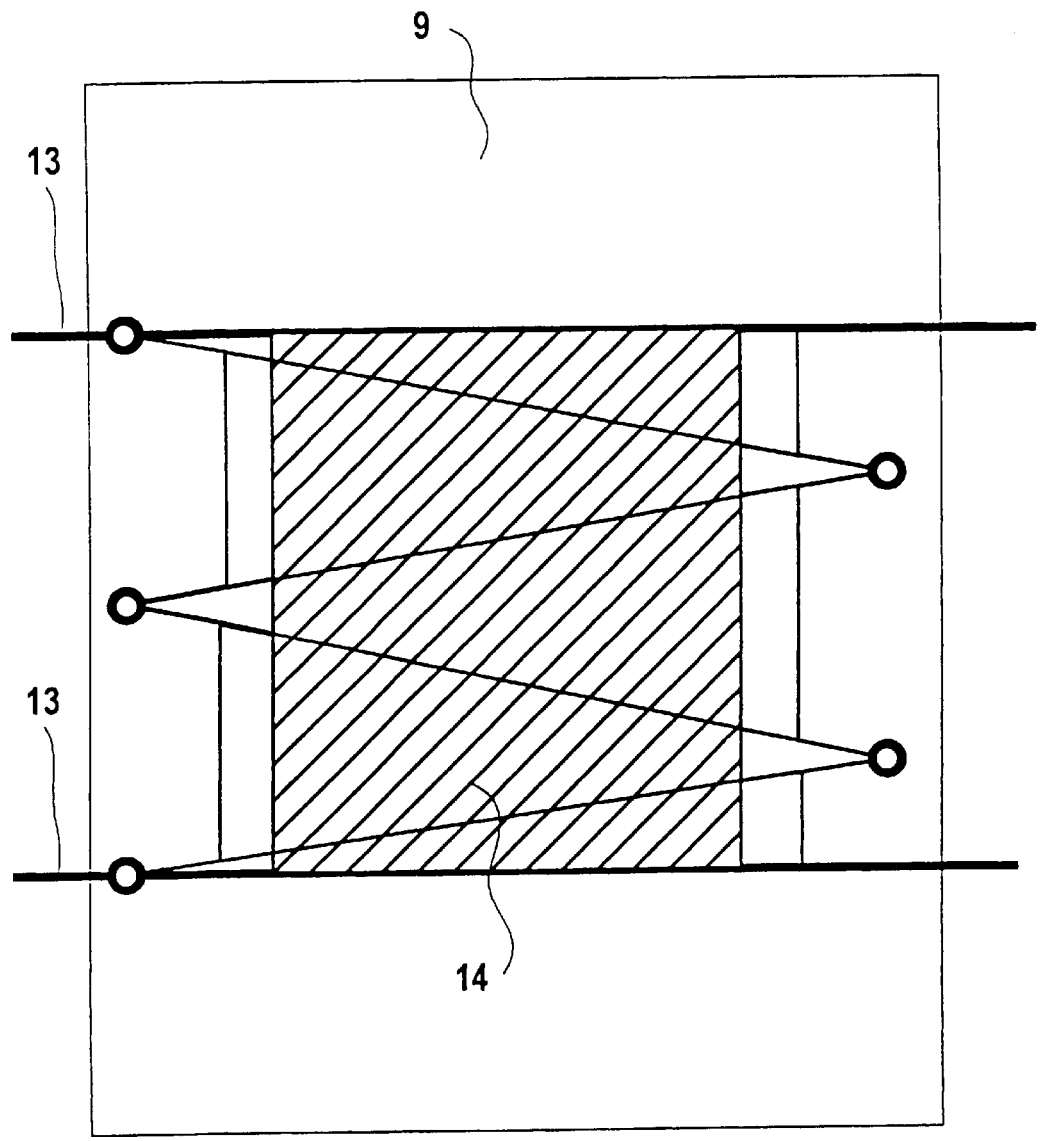
FIG. 4, as noted above, schematically illustrates how integration over the sub-area of interest is conducted in a conventional spiral scan computed tomography system.
Figure 5:
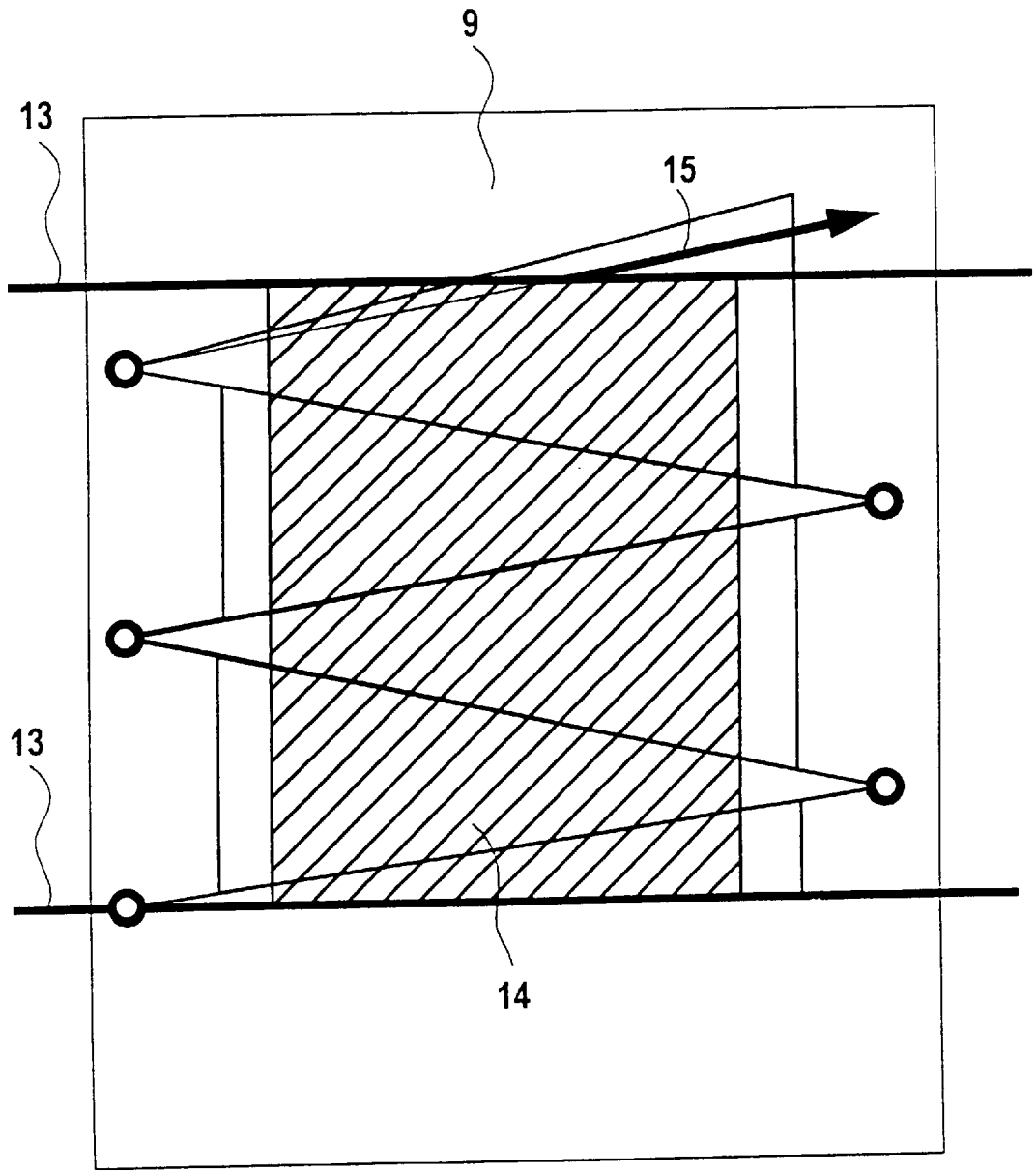
FIG. 5, as noted above, illustrates integration over the sub-area of interest in a conventional spiral scan computed tomography system, under conditions wherein the integral cannot be formed.

This selection of the limiting surfaces assures that the limitation of the sub-area of interest is a straight line—which, moreover, always contains a focus position—for each integration plane that corresponds to a radon value on the φ-plane 16 under consideration. In the inventive method, all plane integrals therefore always can be formed exactly over the sub-areas of interest without the plane integrals being falsified by contributions of regions outside the sub-volume of interest and thus becoming inconsistent, which would result in artifacts. In the inventive method, the plane integration over the sub-areas of interest is accomplished by combining the contributions of different projections, as shown in FIG. 4.

Figure 8:
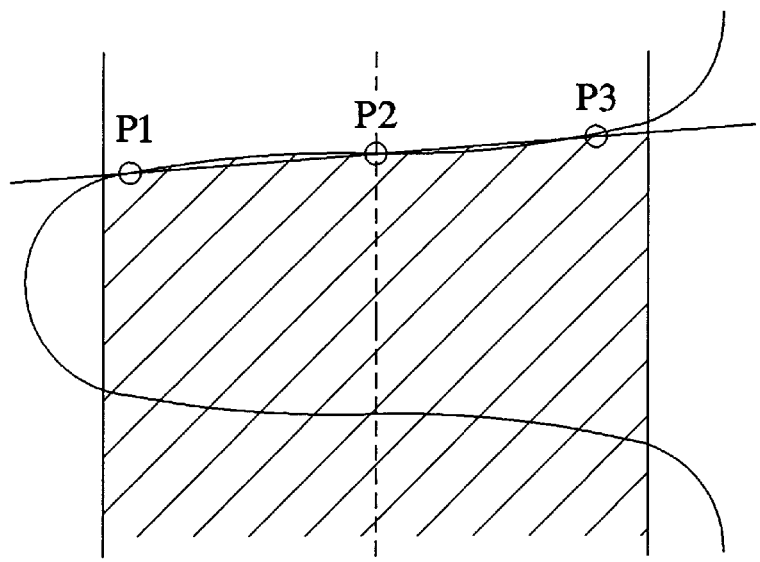
FIGS. 8–9 is a plan view onto the φ-plane or (the integration plane) of an image reconstruction method according to the invention.
Figure 9:
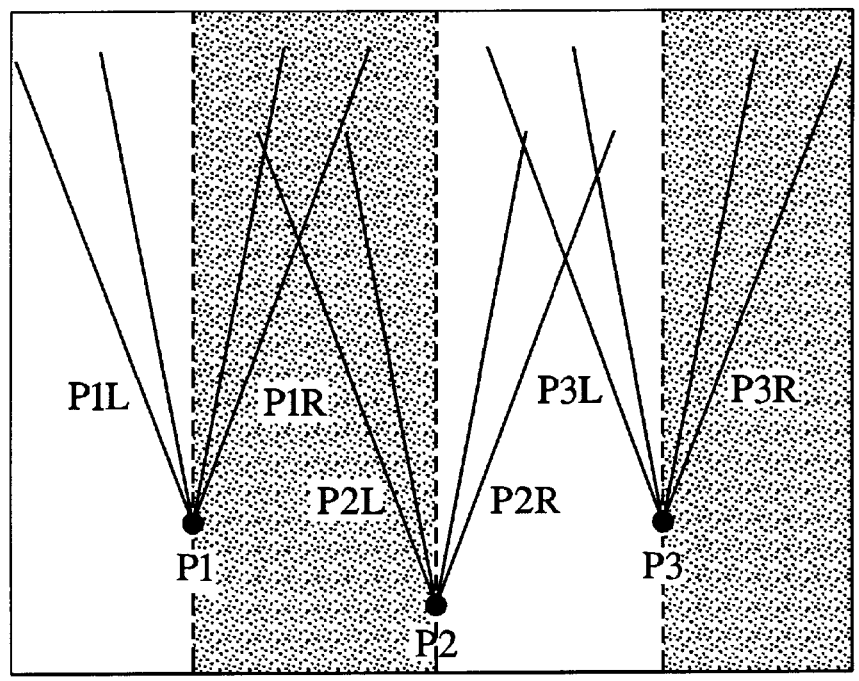

Since the upper and lower limiting surface in the inventive method follows the focus path 12, i.e. are curved, an integration plane can contain a number of separate sub-areas that lie within the sub-volume of interest but are not interconnected. FIGS. 8 and 9 show an example. FIGS. 8 and 9 show an example of an integration plane that contains a number of separate sub-areas that lie within the sub-volume 11 of interest. FIG. 8 shows a plan view onto the φ-plane 16, and FIG. 9 shows a plan view onto the integration plane. The sub-area of interest composed of a number of non-contiguous parts is shown shaded in FIG. 9.

In the inventive method, the integration is limited to the sub-area of interest by virtue of each projection whose focus point lies on the boundary of the sub-volume of interest being divided into two halves by the beam that lies in the integration plane as well as on the boundary of the sub-volume of interest. The left and right halves of these projections are then differently weighted and summed. In FIGS. 8 and 9, the beam fans of the three projections P1, P2 and P3 that lie in the integration plane are divided into a left and a right side by the intersection lines (shown dashed) of the integration plane and the limiting surface of the sub-volume of interest. The sub-fans are P1L, P1R, P2L, P2R, P3L, P3R (L: left, R: right). The plane integral can be calculated over the sub-area of interest by calculating $$0 \cdot P1L + 1 \cdot P1R + 0 \cdot P2L + (-1) \cdot P2R + 0 \cdot P3L + 1 \cdot P3R$$

In general, there are a number of possible weighted linear combinations of the sub-fans that supply the desired plane integral over the sub-area of interest. In the illustrated example, for example, $$(-1) \cdot P1L + 0 \cdot P1R + 1 \cdot P2L + 0 \cdot P2R + 0 \cdot P3L + 1 \cdot P3R$$

would likewise be possible. In the inventive method, that linear combination with the greatest possible statistical dependability, i.e. lowest noise, is selected. The disclosed method has a number of important advantages over known exact methods. The necessity of implementing a circular scan at the start and at the end of the spiral scan, which would be impractical, is eliminated. The memory requirement of the image computer can be reduced by the subdivision of the volume to be reconstructed into many small sub-volumes. The time resolution of the disclosed method is superior to known methods because, given subdivision of the volume to be reconstructed into many small sub-volumes, only one or a few half revolutions of the spiral scan contribute for each sub-volume of interest.

Although various minor modifications might be suggested by those skilled in the art, it should be understood that my wish to embody within the scope of the patent warranted hereon all such modifications as reasonably and properly come with the scope of my contribution to the art.

I claim as my invention:

1. A method for reconstructing an image of an examination subject in a 3D-spherical coordinate system comprising a plurality of φ-planes in an x-ray computed tomography system, comprising the steps of:

conducting a spiral scan of an examination subject by rotating an x-ray beam, having an x-ray beam geometry, around a measurement field in which the examination subject is disposed, said x-ray beam proceeding through a plurality of projections from a plurality of successive focus point locations, said measurement field having a measurement field radius;

detecting x-rays from said x-ray beam attenuated by said examination subject during said spiral scan, said radiation detector producing detector values dependent on the x-rays incident thereon;

conducting line integrations along a plurality of lines over data derived from said detector values to obtain intermediate data;

for each of said φ-planes, calculating 3D radon values representing plane integrals of integration planes containing said straight lines from said intermediate data for a sub-volume of interest defined only for a respective φ-plane and limiting said sub-volume of interest by said measurement field radius and by respective curved surfaces defined by a locus of a straight line proceeding perpendicularly to said respective φ-plane and proceeding from said focus point locations positioned on a spiral segment of said spiral scan.

2. A method as claimed in claim 1 wherein the step of conducting a spiral scan comprises conducting a spiral scan using an x-ray beam having cone beam geometry.

3. A method as claimed in claim 1 wherein the step of conducting a spiral scan comprises conducting a spiral scan using an x-ray beam having pyramidal beam geometry.

4. A method as claimed in claim 1 comprising the additional step of limiting calculation of plane integrals to respective sub-areas of interest, each sub-area of interest being defined as that part of a respective integration plane located inside said sub-volume of interest defined for said respective φ-plane, by dividing projections having a focus point location on one of said curved surfaces into two sub-fans by one of said straight lines lying in the respective integration plane as well as in one of said curved surfaces; and comprising the further step of assembling said sub-area of interest by linear combination of sub-fans.

5. A method as claimed in claim 4 comprising the additional step of selecting a least noise-infested combination as said linear combination of sub-fans.

* * * * *